United States Patent [19]
VanderSyde

[11] 4,132,109
[45] Jan. 2, 1979

[54] BREATH TESTING SYSTEM
[75] Inventor: Gary L. VanderSyde, Naperville, Ill.
[73] Assignee: Alcohol Countermeasure Systems, Inc., Sarnia, Canada
[21] Appl. No.: 818,283
[22] Filed: Jul. 22, 1977
[51] Int. Cl.² ........................... G01N 27/14
[52] U.S. Cl. ................................ 73/23
[58] Field of Search ............... 73/23, 27 R, 421.5 R; 340/237 R; 128/2 C; 23/232 E, 254 E

[56] References Cited
U.S. PATENT DOCUMENTS

| | | | |
|---|---|---|---|
| 3,842,345 | 10/1974 | Padgitt et al. | 128/2 C |
| 3,877,291 | 4/1975 | Hoppesch et al. | 73/27 R |
| 3,886,786 | 6/1975 | Hoppesch et al. | 73/27 R |
| 3,997,837 | 12/1976 | Betz et al. | 73/27 R |

*Primary Examiner*—Stephen A. Kreitman
*Attorney, Agent, or Firm*—Richard G. Kinney

[57] ABSTRACT

In a breath tester of the type wherein a subject blows breath into an input for a predetermined continuous and uninterrupted flow, which breath is exposed to an electronic detector element whose output signal is employed to derive and display an output which is representative of the alcohol present in the breath and which detector, if subject to continued exposure of additional breath after the predetermined flow, is prone to produce an erroneous output, an electronic system is provided for electrically storing and isolating a detector signal produced from only the predetermined flow, whereby errors resulting from continuous flow or mechanical valving arrangements are avoided. The system disclosed includes circuit means for switching out and holding the end of flow detector signal and for producing an output based on that signal.

3 Claims, 1 Drawing Figure

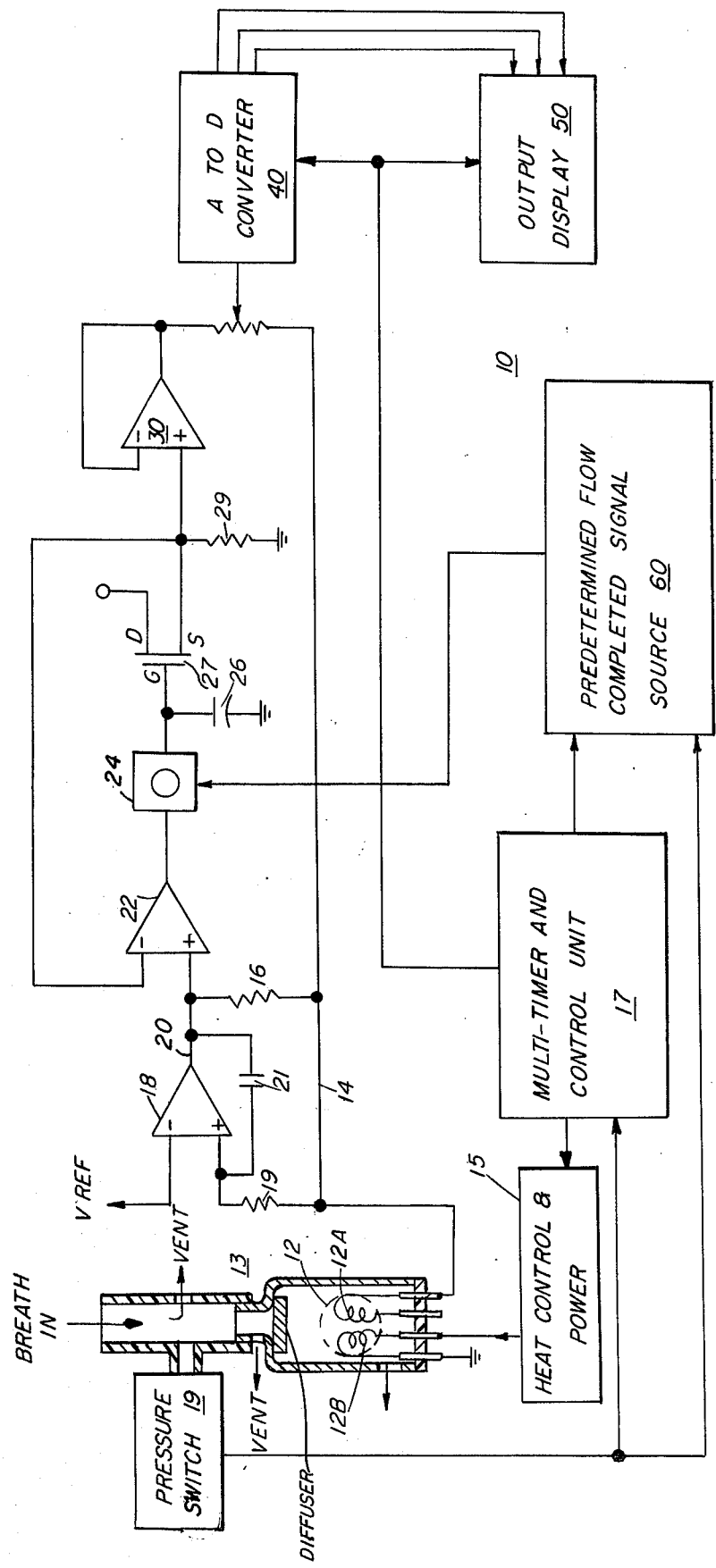

BREATH TESTING SYSTEM

BACKGROUND

Breath testers of the type that employ an electronic detector are of relatively recent origin. These types of testers have many advantages over the older chemical type detectors. Included in these advantages are ease of portability and storage and ease of use. These advantages have led to this type of tester being employed in police work as a "screening" unit as described in U.S. Pat. No. 3,877,291, evidential units and in permanent installations such as coin-operated devices for use by the general public at, for example, drinking establishments.

Testers of this class are described in the following additional U.S. Pat. Nos. 3,764,270; 3,842,345; 3,886,786; 3,823,601; and 3,854,320, all of which are assigned to the same assignee as is the present invention.

In this type of tester it was thought to be necessary to read the peak of the detector output, which peak might occur after the exposure of the breath sample. A problem existed, however, in that the detector is sensitive to breath flow. That is, the output of the detector can vary if the subject continues to blow breath to the detector after the blowing period. Although the operator (e.g., a policeman) should remove the breath input unit and the tester from the subject at the conclusion of the flow, this is not always done or done soon enough, and the result is undesirable differences in outputs depending upon the operator.

One solution, suggested by U.S. Pat. No. 3,886,786 and others, is to provide a solenoid operated valve to stop the flow of breath to the detector at the conclusion of the predetermined flow (normally a time period). However, this approach is difficult and relatively expensive to implement in portable units and leads to problems in operation resulting from electric noise and air movement and vibration resulting from the operation of the valve.

SUMMARY OF THE INVENTION

The present inventor has discovered that good reproducable and consistant results can be obtained without using the absolute peak but instead using the detector output at a consistent point in the predetermined flow. Thus, a breath tester of the type described, constructed and operated in accordance with the present invention includes the improvement of means for storing and electronically isolating the detector output signal after a predetermined flow has occured and for using that isolated and stored signal to produce an output.

This arrangement eliminates the need for a mechanical flow stopping mechanism and solenoid and its associated power and control circuitry and yields the advantage that relatively inexpensive and generally available electronic elements may be substituted for specially designed and relatively expensive flow control elements.

The invention, together with the advantages thereof, may best be understood by reference to the following description taken in connection with the accompanying drawing.

BRIEF DESCRIPTION OF THE DRAWING

The sole FIGURE is a mixed block and circuit diagram of a breath tester of the portable screening type constructed in accordance with the principles of the present invention.

DETAILED DESCRIPTION

Referring to the FIGURE there is depicted a breath tester generally indicated by 10 which includes an electronic detector 12. The detector 12 is preferably of the Taguchi-type, for example, the commercially available Taguchi 109, manufactured by Figaro Engineering, Inc. This particular detector has two internal resistors 12A and 12B, only one of which, 12B, is used as a heater and the other of which is used as an electrode.

After conditioning, the resistance across the elements 12A-12B is a function of the breath and its entrained alcohol to which the detector 12 is exposed.

The detector 12 is positioned in a chamber which forms part of a breath flow system 13 which may be similar to that shown in the aforementioned U.S. Pat. No. 3,877,291. By maintaining the size of the chamber surrounding the detector 12 small, it is possible to condition and purge the detector and chamber by operating only a single heater 12B and this is preferred (although the present invention may be employed in multi heater and air pump systems).

The heater 12B has one end grounded and is powered from a heater control and power circuit 15 which is, in turn controlled by a multi-timer and control unit 17. This timer serves to respond to energization of the tester 10 by, for example, switching on the power switch, by driving the heater control unit 15 to heat the heater 12B for a purge period of, e.g., 120 seconds.

Should, however, breath be blown into the flow system 13 sufficient to close a pressure switch 19 during the purge time period, the time is reset to "zero" and the period started over again.

After the completing of the purge period the tester is presented to a subject who blows into it. The pressure switch 19 then starts a set time period timer (e.g., 5 seconds). If during this period the pressure switch 19 is opened, i.e., if the breath is interrupted during the flow time, then the unit 17 resets the purge timer. At the conclusion of the uninterrupted and continuous flow a predetermined flow signal is produced from source 60.

At the completion of the purge period and the beginning of the exposure of a breath sample the heater is no longer powered so as to lower the temperature of the detector, and the resistance between chassis ground and line 14 is part of a voltage divider network including a resistor 16 connected in series with the inter-electrode resistance of detector 12. The connection point of these two resistors is connected (through a resistor 19) to the negative input of an operational amplifier 18 whose positive input is connected to a source of reference voltage $V_{REF}$.

The amplifier 18 which has a noise subpressing capacitor 21 connected between its output and negative input, functions to increase its output voltage at line 20 so as to raise the voltage of the negative input to match that of the reference voltage. Thus as the resistance across the detector 12 falls the voltage on line 20 increases. This voltage signal is coupled through a second amplifier 22 through a normally conducting CMOS electronic switch 24 to a holding capacitor 26 and the gate of a MOSFET 27. The output of the MOSFET 27 is fed through an operation amplifier 30 to an analog to digital converter 40 and to the Display 50.

The unit 24 is operated to isolate the signal from amplifier 22 from the holding capacitor 26 in response to a predetermined flow complete signal from the source 60. As stated before that signal occurs in this particular embodiment, when the breath pressure switch has been held closed for a set time, e.g. 5 seconds, to insure a good sample of lung breath. (Interruption of the blowing such as to close the pressure switch before this period has run, serves to reset the apparatus and start the purge timing signal).

Isolation of the charge on capacitor 26 from the detector 12 means that any further changes in the detector's output will have no further effects on the eventual output of the tester.

At the end of the flow the output signal from source 60 also serves to energize an A to D convector 40 and display 50 which produce an output dislay depending upon the signal stored on capacitor 26, that is, an output proportioned to the detector output at the end of the flow period.

That is, the voltage at the S terminal of MOSFET 27 is connected through a resistor 29 to ground and also to the positive input of the operational amplifer 30. The D terminal of MOSFET 27 is connected to a source of voltage $V_H$ and the output of operational amplifier 30 is coupled to converter 40 via the tap on potentiometer 31 which is connected from the output of amplifier 30 to line 14.

As an example and with no intent to limit the generality of the invention, one particular breath tester which was constructed and satisfactorily tested employed the following components and values:

Operational Amplifiers 18,22 and 30: MC1458
MOSFET 27: 2N 3796
$V_{REF}$: 2.7 v.
Resistor 19: 4.7K Ohm.
Capacitor 26: 0.22 mfd
Capacitor 21: 0.022 mfd.
Resistor 16: 2.4K Ohm.
Resistor 29: 10K Ohm.
Potentiometer: 10K Ohm.
$V_H$: 8 Volts While one particular embodiment of the invention has been shown and described, it will be obvious to those skilled in the art that changes and modifications may be made without departing from the invention in its broader aspects and therefore, the aim of the appended claims is to cover all such changes and modifications as fall within the true scope and spirit of the invention.

I claim:

1. In a breath tester of the type wherein a subject blows breath into an input for a predetermined continuous and uninterrupted flow, which breath is exposed to an electronic detector whose output signal is representative of the alcohol present in the breath and which detector, if subject to continued exposure of additional breath after the predetermined flow, is prone to produce an erroneous output, the improvement comprising:

circuit means for holding a signal coupled to the detector and responsive thereto;

electronic circuit means, responsive to the sensed completion of a preselected flow for isolating said signal holding circuit means from the detector at the completion of the preselected flow; and means responsive to the stored signal for providing an output indicative of the sensed alcohol in the breath;

whereby continuous exposure of breath to detector after the completing of the predetermined breath flow does not effect the output of the tester.

2. The invention of claim 1 wherein, said electronic circuit means for isolating said signal holding means is responsive to the completion of the predetermined continuous and uninterrupted flow as said preselected flow.

3. The method of obtaining consistant and reproducable results from a breath tester of the type that use an electronic detector whose output signal is representative of the alcohol present in the breath to which it is exposed and which detector if subjected to continued flow of breath after a predetermined flow has been sampled is subject to produce an erroneous output, comprising the steps of:

(a) purging the detector, (b) while the detector is in its purged state, exposing said detector to a breath sample for a preselected fixed testing period of time, which sample is the result of a continuous and uninterrupted flow, and (c) at the conclusion of the preselected fixed testing period of time, storing the signal from the detector, and (d) deriving an output from the stored signal.

* * * * *